US006407097B1

(12) United States Patent
Gayer et al.

(10) Patent No.: US 6,407,097 B1
(45) Date of Patent: Jun. 18, 2002

(54) METHOXIMINOMETHYLOXATHIAZINES

(75) Inventors: Herbert Gayer, Monheim; Peter Gerdes, Aachen; Ulrich Heinemann, Leichlingen; Bernd-Wieland Krüger, Bergisch Gladbach; Klaus Stenzel, Düsseldorf, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/674,354

(22) PCT Filed: Apr. 21, 1999

(86) PCT No.: PCT/EP99/02680

§ 371 (c)(1),
(2), (4) Date: Oct. 30, 2000

(87) PCT Pub. No.: WO99/57116

PCT Pub. Date: Nov. 11, 1999

(30) Foreign Application Priority Data

May 4, 1998 (DE) .......................................... 198 19 828

(51) Int. Cl.$^7$ .................... C07D 419/10; C07D 419/12; A61K 31/506; A61K 31/535; A61K 31/54
(52) U.S. Cl. ......................................... 514/222.5; 544/2
(58) Field of Search ............................ 514/222.5; 544/2

(56) References Cited

U.S. PATENT DOCUMENTS

| 6,103,717 A | 8/2000 | Heinemann et al. ..... 514/229.2 |
| 6,150,521 A | 11/2000 | Gayer et al. .................. 544/65 |
| 6,214,825 B1 | 4/2001 | Krueger et al. .......... 514/229.2 |
| 6,251,899 B1 | 6/2001 | Gerdes et al. ........... 514/229.2 |

FOREIGN PATENT DOCUMENTS

| WO | 96/25406 | 8/1996 |
| WO | 97/27189 | 7/1997 |
| WO | 97/46542 | 12/1997 |
| WO | 99/09026 | 2/1999 |

*Primary Examiner*—John M. Ford
(74) *Attorney, Agent, or Firm*—Joseph C. Gil

(57) ABSTRACT

The invention relates to novel methoximinomethyloxathiazines, to two processes for their preparation and to their use as pesticides.

7 Claims, No Drawings

METHOXIMINOMETHYLOXATHIAZINES

The invention relates to novel methoximinomethyloxathiazines, to two processes for their preparation and to their use as pesticides.

Certain methoximinomethyloxathiazines having a similar substitution pattern, and their fungicidal action, have already been disclosed (WO 96-25406). However, the action of these prior-art compounds is, in particular at low application rates and concentrations, not entirely satisfactory in all areas of use.

This invention, accordingly, provides the novel methoximinomethyloxathiazines of the general formula (I)

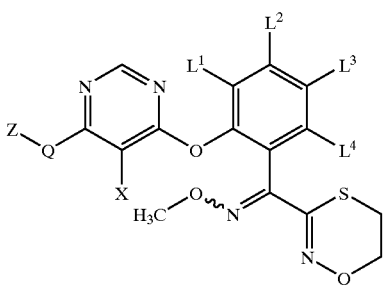

(I)

in which

Z represents in each case optionally substituted cycloalkyl, aryl, arylalkyl, heterocyclyl or heterocyclylalkyl, Q represents oxygen or sulphur, X represents halogen and $L^1$, $L^2$, $L^3$ and $L^4$ are identical or different and, independently of one another, each represent hydrogen, halogen, cyano, nitro, in each case optionally halogen-substituted alkyl, alkoxy, alkylthio, alkylsulphinyl or alkylsulphonyl.

In the definitions, the saturated or unsaturated hydrocarbon chains, such as alkyl, alkanediyl, alkenyl or alkinyl, are in each case straight-chain or branched, including in combination with heteroatoms, such as, for example, an alkoxy, alkylthio or alkylamino.

Aryl represents aromatic, mono- or polycyclic hydrocarbon rings, such as, by way of example and preferably, phenyl, naphthyl, anthranyl, phenanthryl, preferably phenyl or naphthyl, in particular phenyl.

Heterocyclyl represents saturated or unsaturated, and also aromatic, cyclic compounds in which at least one ring member is a heteroatom, i.e. an atom other than carbon. If the ring contains a plurality of heteroatoms, these may be identical or different. Preferred heteroatoms are oxygen, nitrogen or sulphur. If appropriate, the cyclic compounds form, together with other carbocyclic or heterocyclic fused-on or bridged rings, a polycyclic ring system. Preference is given to mono- or bicyclic ring systems, in particular to mono- or bicyclic aromatic ring systems.

Cycloalkyl represents saturated carbocyclic annular compounds which, if appropriate, form a polycyclic ring system with other carbocyclic fused-on or bridged rings.

Furthermore, it has been found that the novel methoximinomethyloxathiazines of the general formula (I) are obtained when a) 3-(2-hydroxyphenyl)-3-methoxyiminomethyl-oxathiazines of the formula (II)

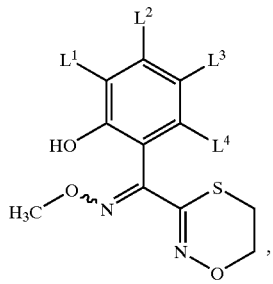

(II)

in which $L^1$, $L^2$, $L^3$ and $L^4$ are each as defined above, are reacted with a substituted halogenopyrimidine of the general formula (III)

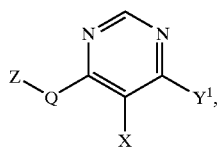

(III)

in which

Z, Q and X are each as defined above and $Y^1$ represents halogen, if appropriate in the presence of a diluent, if appropriate in the presence of an acid acceptor and if appropriate in the presence of a catalyst, or when b) phenoxypyrimidines of the general formula (IV)

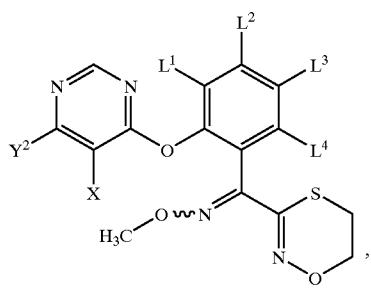

(IV)

in which

X, $L^1$, $L^2$, $L^3$ and $L^4$ are each as defined above an $Y^2$ are presents halogen are reacted with a cyclic compound of the general formula (V)

Z—Q—H (V)

in which

Z and Q are each as defined above, if appropriate in the presence of a diluent, if appropriate in the presence of an acid acceptor and if appropriate in the presence of a catalyst.

Finally, it has been found that the novel methoximinomethyloxathiazines of the general formula (I) have very strong microbicidal action.

If appropriate, the compounds according to the invention can be present as mixtures of various possible isomeric forms, in particular of steroisomers, such as, for example, E and Z. What is claimed are both the E and the Z isomers, and any mixtures of these isomers.

The invention preferably provides compounds of the formula (I) in which

Z represents cycloalkyl or cycloalkylalkyl having in each case 3 to 7 carbon atoms in the cycloalkyl moiety and 1 to 4 carbon atoms in the alkyl moiety, each of which is optionally mono- or disubstituted by halogen or alkyl;

represents heterocyclyl or heterocyclylalkyl having in each case 3 to 7 ring members and 1 to 4 carbon atoms in the alkyl moiety, each of which is optionally substituted by halogen or alkyl having 1 to 4 carbon atoms;

or represents aryl or arylalkyl having in each case 6 to 10 carbon atoms in the aryl moiety and 1 to 4 carbon atoms in the alkyl moiety, each of which is optionally mono- to tetrasubstituted in the aryl moiety by identical or different substituents, where the possible substituents are preferably selected from the list below:

halogen, cyano, nitro, amino, formyl, carbamoyl, thiocarbamoyl;

in each case straight-chain or branched alkyl, alkoxy, alkoxyalkyl, alkylthioalkyl, alkylaminoalkyl, dialkylaminoalkyl, alkylthio, alkylsulphinyl or alkyl sulphonyl having in each case 1 to 8 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkylcarbonyl, alkoxycarbonyl, alkylaminocarbonyl, dialkylaminocarbonyl, arylalkylaminocarbonyl, alkenylcarbonyl or alkinylcarbonyl, having 1 to 6 carbon atoms in the respective hydrocarbon chains;

cycloalkyl or cycloalkyloxy having in each case 3 to 6 carbon atoms;

in each case doubly attached alkylene having 3 or 4 carbon atoms, oxyalkylene having 2 or 3 carbon atoms or dioxyalkylene having 1 or 2 carbon atoms, each of which is optionally mono- to tetrasubstituted by identical or different substituents selected from the group consisting of fluorine, chlorine, oxo, methyl, trifluoromethyl and ethyl;

or a grouping

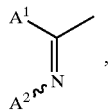

in which
A¹ represents hydrogen or alkyl having 1 to 4 carbon atoms or cycloalkyl having 3 to 6 carbon atoms and
A² represents hydroxyl, amino, methylamino, methyl, phenyl, benzyl, alkoxy, alkylamino, dialkylamino having 1 to 4 carbon atoms in the respective alkyl chains, Q represents oxygen or sulphur, X represents fluorine, chlorine or bromine, preferably fluorine or chlorine and in particular fluorine and L¹, L², L³ and L⁴ are identical or different and, independently of one another, each represents hydrogen, halogen, cyano, nitro, represents alkyl, alkoxy, alkylthio, alkylsulphinyl or alkylsulphonyl having in each case 1 to 6 carbon atoms and being in each case optionally substituted by 1 to 5 halogen atoms, preferably represents hydrogen or methyl and in particular hydrogen.

The invention relates in particular to compounds of the formula (I) in which

Z represents cyclopentyl or cyclohexyl, each of which is optionally mono- or disubstituted by fluorine, chlorine, methyl, ethyl or hydroxyl;

represents thienyl, pyridyl, furyl, thienylmethyl, pyridylmethyl or furylmethyl, each of which is optionally substituted by methyl, ethyl, fluorine, chlorine or bromine;

or, in particular, represents phenyl or benzyl, each of which is optionally mono- to tetrasubstituted, in particular mono- or disubstituted, by identical or different substituents, where the possible substituents are preferably selected from the list below:

fluorine, chlorine, bromine, cyano, nitro, amino, formyl, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propene-1-yl, crotonyl, propargyl, vinyloxy, allyloxy, 2-methylallyloxy, propene-1-yloxy, crotonyloxy, propargyloxy;

trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, acryloyl, propioloyl, cyclopentyl, cyclohexyl, in each case doubly attached propanediyl, ethyleneoxy, methylenedioxy, ethylenedioxy, each of which is optionally mono- to tetrasubstituted by identical or different substituents selected from the group consisting of fluorine, chlorine, oxo, methyl and trifluoromethyl or a grouping,

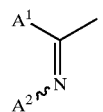

where
A¹ represents hydrogen or methyl and
A² represents hydroxyl, methoxy, ethoxy, amino, methylamino, methyl, phenyl or benzyl, Q represents sulphur or, in particular, oxygen, X represents fluorine or chlorine, in particular fluorine and $L^1$, $L^2$, $L^3$ and $L^4$ are identical or different and, independently of one another, each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, preferably hydrogen or methyl and in particular hydrogen.

Particular preference is given to compounds of the formula (I) in which

Q represents oxygen.

Particular preference is given to compounds of the formula (I) in which $L^1$, $L^2$, $L^3$ and $L^4$ each represent hydrogen.

Particular preference is given to compounds of the formula (I) in which

X represents fluorine.

Particular preference is given to compounds of the formula (I) in which

Z represents unsubstituted or substituted phenyl. Preferred substituents are halogen, alkyl, cyano and alkyloxy radicals.

The abovementioned general or preferred radical definitions apply both to the end products of the formula (I) and, correspondingly, to the starting materials and intermediates required in each case for the preparation.

Independently of the combination given in each case, the definitions of radicals given in the combinations or preferred combinations of radicals in question specifically for these radicals can also be replaced by definitions of radicals of other preferred ranges.

These radical definitions can be combined with one another at will, i.e. including combinations between the given ranges of preferred compounds.

The formula (II) provides a general definition of the 3-(2-hydroxyphenyl)-3-methoxyiminomethyl-oxathiazines required as starting materials for carrying out the process a) according to the invention. In this formula (II), $L^1$, $L^2$, $L^3$ and $L^4$ each preferably or in particular have those meanings which have already been mentioned in connection with the description of the compounds of the formula (I) according to the invention as being preferred or as being particularly preferred for $L^1$, $L^2$, $L^3$ and $L^4$.

The starting materials of the formula (II) are novel and also form part of the subject matter of the present application.

They are obtained (process c) when acylthioethylbenzofurandione dioximes of the general formula (VI)

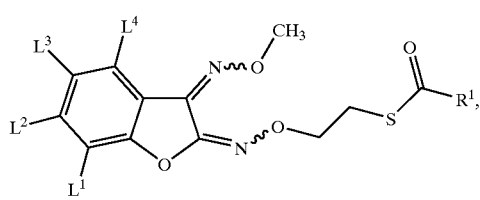

(VI)

in which $L^1$, $L^2$, $L^3$ and $L^4$ are each as defined above and $R^1$ represents alkyl are reacted with a base, if appropriate in the presence of a diluent.

The formula (VI) provides a general definition of the acylthioethylbenzofurandione dioximes required as starting materials for carrying out the process c) according to the invention. In this formula (VI), $L^1$, $L^2$, $L^3$ and $L^4$ each preferably or in particular have those meanings which have already been mentioned in connection with the description of the compounds of the formula (I) according to the invention as being preferred or as being particularly preferred for $L^1$, $L^2$, $L^3$ and $L^4$. $R^1$ represents alkyl, preferably methyl or ethyl.

The starting materials of the formula (VI) are novel and also form part of the subject-matter of the present application.

They are obtained (process d) when benzofurandione dioximes of the general formula (VII)

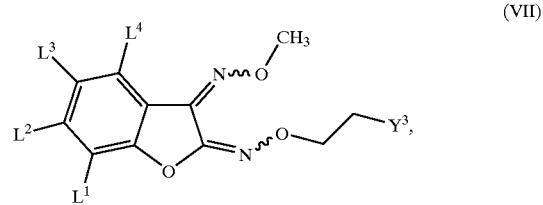

(VII)

in which $L^1$, $L^2$, $L^3$ and $L^4$ are each as defined above and $Y^3$ represents halogen, alkylsulphonyloxy or arylsulphonyloxy are reacted with a thiocarboxylic acid of the general formula (VIII)

(VIII)

in which $R^1$ is as defined above, if appropriate in the presence of a diluent and if appropriate in the presence of a base.

The formula (VII) provides a general definition of the benzofurandione dioximes required as starting materials for carrying out the process d) according to the invention. In this formula (VII), $L^1$, $L^2$, $L^3$ and $L^4$ each preferably or in particular have those meanings which have already been mentioned in connection with the description of the compounds of the formula (1) according to the invention as being preferred or as being particularly preferred for $L^1$, $L^2$, $L^3$ and $L^4$. $Y^3$ represents halogen, preferably represents chlorine or bromine, or represents alkylsulphonyloxy or arylsulphonyloxy, preferably methylsulphonyloxy, benzylsulphonyloxy or tolylsulphonyloxy.

The starting materials of the formula (VII) are obtained when hydroxyethylbenzofurandione dioximes of the formula (IX)

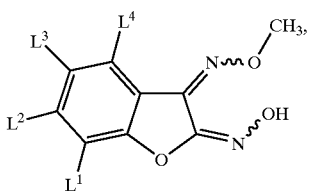

(IX)

in which

L¹, L², L³ and L⁴ are each as defined above, are reacted with an ethane derivative, such as, for example, dibromoethane or bis-methylsulphonyl-ethane-1,2-diol, if appropriate in the presence of a diluent, such as, for example, dimethylformamide or N-methylpyrrolidone, and if appropriate in the presence of a base, such as, for example, sodium carbonate or potassium carbonate.

The starting materials of the formula (IX) are known or can be prepared by known processes (compare WO 97-46542).

The thiocarboxylic acids furthermore required as starting materials for carrying out the process d) according to the invention are generally known chemicals for synthesis.

The formula (III) provides a general definition of the halogenopyrimidines furthermore required as starting materials for carrying out the process a) according to the invention. In this formula (III), Z, Q and X each preferably or in particular have those meanings which have already been mentioned in connection with the description of the compounds of the formula (I) according to the invention as being preferred or as being particularly preferred for Z, Q and X. Y¹ represents halogen, preferably fluorine or chlorine.

The starting materials of the formula (III) are known (compare, for example, DE-A 4340181; Chem.Ber., 90(1957), 942, 951), and/or they can be prepared by known methods, for example by reacting the trihalogenopyrimidines of the formula (XIII) (see below) with cyclic compounds of the formula (V) (see below).

The formula (IV) provides a general definition of the phenoxypyrimidines required as starting materials for carrying out the process b) according to the invention. In this formula (IV), X, L¹, L², L³ and L⁴ each preferably or in particular have those meanings which have already been mentioned in connection with the description of the compounds of the formula (I) according to the invention as being preferred or as being particularly preferred for X, L¹, L², L³ and L⁴. Y² represents halogen, preferably fluorine or chlorine.

The starting materials of the formula (IV) are novel and also form part of the subject-matter of the present application.

The phenoxypyrimidines of the general formula (IV) are obtained (process e) when 3-(2-hydroxyphenyl)-3-methoxyiminomethyl-oxathiazines of the formula (II) are reacted with a trihalogenopyrimidine of the general formula (XIII)

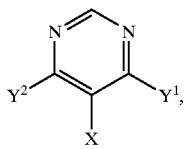

(XIII)

in which

X, Y¹ and Y² are identical or different and each represent halogen, if appropriate in the presence of a diluent, if appropriate in the presence of an acid acceptor and if appropriate in the presence of a catalyst.

The 3-(2-hydroxyphenyl)-3-methoxyiminomethyl-oxathiazines of the formula (II) required as starting materials for carrying out the process e) according to the invention have already been described in connection with the description of the process a) according to the invention.

The formula (XIII) provides a general definition of the trihalogenopyrimidines furthermore required as starting materials for carrying out the process e) according to the invention. In this formula (XIII), X, Y¹ and Y² each represent halogen, preferably fluorine or chlorine.

The trihalogenopyrimidines of the formula (XIII) are known and/or can be prepared by known methods (compare, for example, Chesterfield et al., J. Chem. Soc., 1955; 3478, 3480; WO 97-27189).

The formula (V) provides a general definition of the cyclic compounds furthermore required as starting materials for carrying out the process b) according to the invention. In this formula (V), Z and Q each preferably or in particular have those meanings which have already been mentioned in connection with the description of the compounds of the formula (I) according to the invention as being preferred or as being particularly preferred for Z and Q.

The cyclic compounds of the formula (V) are known chemicals for synthesis, or they can be prepared by simple methods.

Suitable diluents for carrying out the processes a), b) and e) according to the invention are all inert organic solvents. These preferably include ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; nitrites, such as N,N-acetonitrile, propionitrile, n- or i-butyronitrile or benzonitrile; amides, such as dimethylformamide, N,N-dimethylacetamide, N-methylformanilide, N-methylpyrrolidone or hexamethylphosphoric triamide; sulphoxides, such as dimethyl sulphoxide; or sulphones, such as sulpholane.

Suitable diluents for carrying out the process c) according to the invention are all inert organic solvents. These preferably include ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; amides, such as N,N-dimethylformamide, N,N-dimethylacetamide, N-methylformanilide, N-methylpyrrolidone or hexamethylphosphoric triamide; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

Suitable diluents for carrying out the process e) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; ketones, such as acetone, butanone, methyl isobutyl ketone or cyclohexanone; nitriles, such as acetonitrile, propionitrile, n- or i-butyronitrile or benzonitriles; amides, such as N,N-dimethylformamide, N,N-dimethylacetamide, N-methylformanilide, N-methyl-pyrrolidone or hexamethylphosphoric triamide; esters, such as methyl acetate or ethyl acetate; sulphoxides, such as dimethyl sulphoxide; sulphones, such as sulpholane.

The processes a), b), c), d) and e) according to the invention are, if appropriate, carried out in the presence of a suitable base. Suitable bases are all customary inorganic or organic bases. These preferably include alkaline earth metal, or alkali metal hydrides, hydroxides, alkoxides, carbonates or bicarbonates, such as, for example, sodium hydride, sodium amide, potassium tert-butoxide, sodium hydroxide, potassium hydroxide, sodium carbonate, potassium carbonate, potassium bicarbonate or sodium bicarbonate.

Suitable catalysts for the processes a), b) and e) according to the invention are all copper (I) salts, such as, for example, copper(I) chloride, copper(I) bromide or copper(I) iodide.

When carrying out the processes a), b) and e) according to the invention, the reaction temperatures can be varied within a relatively wide range. In general, the reactions are carried out at temperatures from −20° C. to 100° C., preferably at temperatures from −10° C. to 80° C.

When carrying out the process c) according to the invention, the reaction temperatures can be varied within a relatively wide range. In general, the reaction is carried out at temperatures from 20° C. to 250° C., preferably at temperatures from 50° C. to 150° C.

When carrying out the process d) according to the invention, the reaction temperatures can be varied within a relatively wide range. In general, the reaction is carried out at temperatures from −20° C. to 100° C., preferably at temperatures from −10° C. to 80° C.

For carrying, out the process a) according to the invention for preparing the compounds of the formula (I), generally 0.5 to 15 mol, preferably 0.8 to 8 mol of substituted halogenopyrimidine of the formula (III) are employed per mole of the 3-(2-hydroxyphenyl)-3-methoxyiminomethyl-oxathiazine of the formula (II).

For carrying, out the process b) according to the invention for preparing the compounds of the formula (I), generally 0.5 to 15 mol, preferably 0.8 to 8 mol of a cyclic compound of the general formula (V) are employed per mole of the phenoxypyrimidine of the formula (IV).

For carrying out the process d) according to the invention for preparing the compounds of the formula (VI), generally 1 to 15 mol, preferably 1 to 8 mol, of thiocarboxylic acid of the formula (VIII) are employed per mole of benzofurandione dioxime of the formula (VII).

For carrying out the process f) according to the invention for preparing the compounds of the formula (IV), generally 1 to 15 mol, preferably 2 to 8 mol, of a trihalogenopyrimidine of the general formula (XIII) are employed per mole of the 3-(2-hydroxyphenyl)-3-methoxyiminomethyl-oxathiazine of the formula (II).

In general, the processes a), b), c), d) and e) according to the invention are carried out under atmospheric pressure. However, it is also possible to operate under elevated or reduced pressure—in general between 0.1 bar and 10 bar.

The practice of the reaction, the work-up and the isolation of the reaction products are carried out by generally customary processes (compare also the Preparation Examples).

The substances according to the invention have potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;* and

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in fruit and vegetable growing and viticulture, such as, for example, against Sphaerotheca species.

The active compounds according to the invention are also suitable for increasing the yield of crops. Moreover, they have reduced toxicity and are tolerated well by crops.

In the protection of materials, the substances according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:
Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,* and
Staphylococcus, such as *Staphylococcus aureus.*

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to use for example organic solvents as auxiliary solvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins, and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:
Fungicides
aldimorph, ampropylfos, ampropylfos potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1 H-1,2,4-triazol-1-yl)-3-octanone, (E)-α-(methoxyimino)-N-methyl-2-phenoxy-phenylacetamide, isopropyl{2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1 H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano-[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro [4.5]decane-2-methanamine, 8-hydroxyquinoline sulphate, 9H-xanthene-2-[(phenylamnino)-carbonyl]-9-carboxylic hydrazide, bis-(1-methylethyl)-3-methyl-4-[(3-methylbenzoyl)oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholinehydrochloride, ethyl[(4-chlorophenyl)-azo]-cyanoacetate, potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-mono-sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
Bactericides
bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides
abamectin, acephate, acrinathrin, alanycarb, aldicarb, alphamethrin, amitraz, avermectin, AZ 60541, azadirachtin, azinphos A, azinphos M, azocyclotin, *Bacillus thuringiensis,* 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton,
edifenphos, emamectin, esfenvalerate, ethiofencarb, ethion, ethofenprox, ethoprophos, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mevinphos, mesulfenphos, metaldehyde, methacrifos, methamidophos, methidathion, methiocarb, methomyl, metolcarb, milbemectin, monocrotophos, moxidectin,
naled, NC 184, nitenpyram,
omethoate, oxamyl, oxydemethon M, oxydeprofos,
parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen,
quinalphos,
salithion, sebufos, silafluofen, sulfotep, sulprofos,
tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, zetamethrin.

It is also possible to admix other known active compounds, such as herbicides, fertilizers and growth-promoting substances.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is further possible to apply the active compounds by the ultra-low-volume method or to inject the active compound formulation, or the active compound itself, into the soil. The seed of the plants can also be treated.

When using the active compounds according to the invention as fungicides, the application rates can be varied within a relatively wide range, depending on the type of application. In the treatment of parts of plants, the application rates of active compound are generally between 0.1 and 10,000 g/ha, preferably between 10 and 1000 g/ha. In the treatment of seed, the application rates of active compound are generally between 0.001 and 50 g per kilogram of seed, preferably between 0.01 and 10 g per kilogram of seed. In the treatment of the soil, the application rates of active compound are generally between 0.1 and 10,000 g/ha, preferably between 1 and 5000 g/ha.

The compositions used for the protection of industrial materials generally comprise an amount of 1 to 95%, preferably 10 to 75%, of the active compounds.

The use concentrations of the active compounds according to the invention depend on the species and the occurrence of the microorganisms to be controlled and on the composition of the material to be protected. The optimal rate of application can be determined by test series. In general, the use concentrations are in the range from 0.001 to 5% by weight, preferably 0.05 to 1.0% by weight, based on the material to be protected.

The activity and the activity spectrum of the active compounds to be used according to the invention in the protection of materials, or of the compositions, concentrates or quite generally formulations prepared therefrom, can be increased by adding, if appropriate, other antimicrobially active compounds, fungicides, bactericides, herbicides, insecticides or other active compounds to widen the activity spectrum or to obtain particular effects, such as, for example, additional protection against insects. These mixtures may have a wider spectrum of activity than the compounds according to the invention.

Cereal diseases, such as, for example, Leptosphaeria species, or rice diseases, such as, for example, Pyricularia species, are also controlled successfully.

PREPARATION EXAMPLES

Example 1

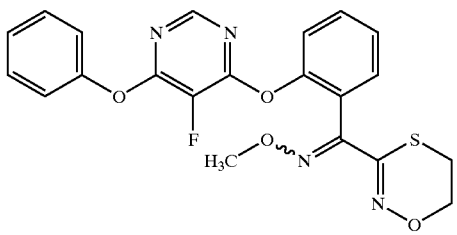

Process a)

With cooling, 0.12 g (0.004 mol) of 80% strength sodium hydride is added to a mixture of 1 g (0.004 mol) of (5,6-dihydro-[1,4,2]oxathiazin-3-yl)-(2-hydroxy-phenyl)-methanone O-methyloxime and 0.85 g (0.0041 mol) of 4-phenoxy-5,6-di-fluoropyrimidine in 10 ml of dimethylformamide, and the mixture is stirred at 25° C. for 12 hours. The reaction mixture is poured into water and extracted with ethyl acetate, the organic phase is dried over sodium sulphate and the solvent is distilled off under reduced pressure. The residue is chromatographed over silica gel using cyclohexane/ethyl acetate (1:1). This gives 0.9 g (51% of theory) of (5,6-dihydro-[1,4,2]-oxathiazin-3-yl)-2-[(5-fluoro-6-phenoxy-pyrimidine-4-yloxy)-phenyl]-methanone O-methyloxime.

$^1$H NMR spectrum (CDCl$_3$/TMS): δ=3.17/3.18/3.19/3.20 (2H); 3.85 (3H); 4.13/4.14/4.15/4.16 (2H); 7.19–7.51 (9H); 8.09 (1H) ppm.

Example 2

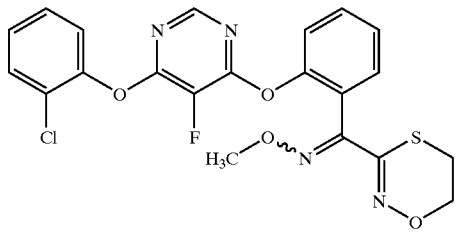

Process b)

At 25° C., 0.62 g (0.0045 mol) of potassium carbonate is added to a mixture of 1.5 g (0.0041 mol) of [2-(5,6-difluoro-pyrimidine-4-yloxy)-phenyl]-(5,6-dihydro-[1,4,2] oxathiazin-3-yl)-methanone O-methyloxime and 0.52 g (0.004 mol) of 2-chlorophenol in 15 ml of acetonitrile, and the mixture is stirred at 25° C. for 12 hours. The reaction mixture is poured into water and extracted with ethyl acetate, the organic phase is dried over sodium sulphate and the solvent is distilled off under reduced pressure.

This gives 1.4 g (73.6%) of crude (5,6-dihydro-[1,4,2] oxathiazin-3-yl)-{2-[5-fluoro-6-(2-chlorophenoxy)-pyrimidine-4-yloxy]-phenyl}-methanone O-methyloxime.

$^1$H NMR spectrum (CDCl$_3$/TMS): δ=3.17/3.18/3.19/3.20 (2H); 3.84 (3H); 4.13/4.14/4.15/4.16 (2H); 7.19–7.52 (8H); 8.06 (1H) ppm.

The compounds of the formula (I-a) listed in Table 1 below are obtained by the methods of Examples 1 and 2, and in accordance with the specifications of the general description of the processes.

TABLE 1

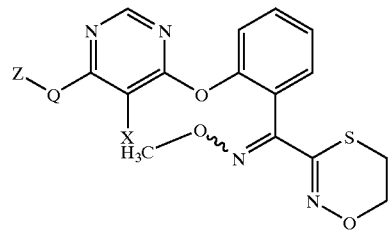

| Example | Z | Q | X | m.p. (° C.) | NMR* | logP** | Process |
|---|---|---|---|---|---|---|---|
| 3 | 2-methyl-3-chlorophenyl | O | F | 62–65 | 3.85 | 4.33 | a) |
| 4 | 2-allyloxyphenyl | O | F | | 3.85 | 4.16 | a) |
| 5 | 2,3-dichlorophenyl | O | F | | 3.84 | 4.23 | a) |
| 6 | 2-cyanophenyl | O | F | | 3.86 | 3.27 | a) |
| 7 | 2-methylphenyl | O | F | 115–17 | 3.85 | 3.82 | a) |
| 8 | 2-fluorophenyl | O | F | | 3.84 | 3.61 | b) |
| 9 | phenyl | S | F | | | 3.89 | b) |
| 10 | 2-bromophenyl | O | F | | | 3.83 | b) |

TABLE 1-continued

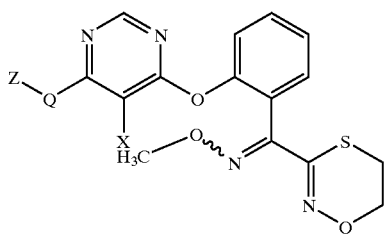

| Example | Z | Q | X | m.p. (° C.) | NMR* | logP** | Process |
|---------|---|---|---|-------------|------|--------|---------|

*) The ¹H NMR spectra were recorded in deuterochloroform (CDCl₃) or hexadeuterodimethyl sulphoxide (DMSO-d₆) using tetramethylsilane (TMS) as internal standard. The chemical shift is stated as δ value in ppm.
**) The logP values were determined in accordance with the EEC directive 79/831 Annex V. A8 by HPLC (gradient method, acetonitrile/0.1% aqueous phosphoric acid)

Preparation of the Starting Materials of the Formula (IV)

Example (IV-1)

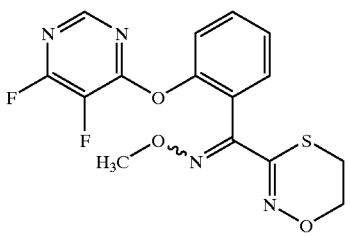

Process e)

2.52 g (0.01 mol) of (5,6-dihydro-[1,4,2]oxathiazin-3-yl)-(2-hydroxyphenyl)-methanone O-methyloxime are dissolved in 10 ml of acetonitrile and admixed with 1.7 g (0.0123 mol) of potassium carbonate. The mixture is then cooled with stirring to 0° C., and 1.34 g (0.01 mol) of 4,5,6-trifluoropyrimidine are then added. Without further cooling, the mixture is stirred for another 12 hours. The solvent is then distilled off under reduced pressure and the residue is poured into water and extracted with ethyl acetate. The organic phase is dried over sodium sulphate and the solvent is distilled off under reduced pressure. This gives 2.3 g (62% of theory) of [2-(5,6-difluoro-pyrimidine-4-yloxy)-phenyl]-(5,6-dihydro-[1,4,2]oxathiazin-3-yl)-methanone O-methyloxime.

¹H NMR spectrum (CDCl₃/TMS): δ=3.15/3.16/3.17/3.18 (2H); 3.83 (3H); 4.11/4.12/4.13/4.14 (2H); 7.26–7.53 (4H); 8.20 (1H) ppm.

HPLC: log P=2.80.

Preparation of the Starting Materials of the Formula (II) Example (II-1)

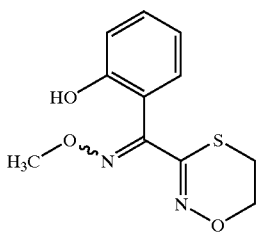

Process c) 3.67 g (0.0125 mol) of S-[2-(3-methoxyimino-3H-benzofuran-2-ylideneaminooxy)-ethyl] thioacetate in 40 ml of methanol are heated under reflux with 12.5 ml of 2N aqueous potassium hydroxide solution for 15 minutes. The solvent is then distilled off under reduced pressure and the residue is admixed with 2N aqueous hydrochloric acid. The mixture is extracted with diethyl ether, the organic phase is dried over sodium sulphate and the solvent is distilled off under reduced pressure. The residue is stirred with diethyl ether, giving 0.78 g (24.7% of theory) of (5,6-dihydro-[1,4,2]oxathiazin-3-yl)-(2-hydroxyphenyl)-methanone O-methyloxime.

¹H NMR spectrum (CDCl₃/TMS): δ=3.21/3.22/3.23/3.24 (2H); 4.06 (3H); 4.18/4.19/4.20/4.21 (2H); 6.3 (1H, b); 6.93–6.98 (2H); 7.17–7.21 (1 H); 7.26–7.34 (1H) ppm. HPLC: log P=1.75.

Preparation of the Starting Materials of the Formula (VI)

Example (VI-1)

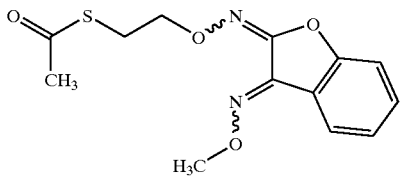

Process d)
4.15 g (0.0138 mol) of benzofuran-2,3-dione 2-[O-(2-bromoethyl)-oxime] 3-(O-methyloxime) are dissolved in 14 ml of N,N-dimethylformamide. At 20° C., 1.6 g (0.021 mol) of thioacetic acid and 2.3 g (0.021 mol) of sodium carbonate are added, and the mixture is stirred for 2 hours. The reaction mixture is then poured into water and extracted with diethyl ether. The organic phase is dried over sodium sulphate and the solvent is distilled off under reduced pressure.

This gives 3.97 g (95.7% of theory) of crude S-[2-(3-methoxyimino-3H-benzofuran-2-ylideneaminooxy)-ethyl] thioacetate, which is reacted further without any purification, as a mixture of stereoisomers.

Isomer A
  HPLC: log P=3.01
  $^1$H NMR spectrum (CDCl$_3$/TMS): δ=4.22 (3H) ppm.
Isomer B
  HPLC: log P=3.18.
  $^1$H NMR spectrum (CDCl$_3$/TMS): δ=4.21 (3H) ppm.

Preparation of a Starting Material of the Formula (VII)

Example VII-1

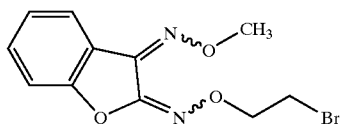

1 g (0.0052 mol) of benzofuran-2,3-dione 3-(O-methyloxime) 2-oxime with 1.5 g (0.0141 mol) of sodium carbonate and 3 g (0.016 mol) of 1,2-dibromoethane in 5 ml of dimethylformamide are stirred at 80° C. for 6 hours. The reaction mixture is subsequently poured into water and extracted with diethyl ether. The organic phase is washed with aqueous potassium hydroxide solution and dried over sodium sulphate. The solvent is distilled off under reduced pressure, giving 1.1 g (70.7% of theory) of crude benzofuran-2,3-dione 2-[O-(2-bromoethyl)-oxime] 3-(O-methyloxime) as a mixture of stereoisomers which is reacted further without any purification.

Isomer A:
  HPLC log P=3.08
  $^1$H NMR spectrum (CDCl$_3$/TMS): δ=4.23 (3H) ppm
Isomer B:
  HPLC log P=3.23
  $^1$H NMR spectrum (CDCl$_3$/TMS): δ=4.21 (3H) ppm.

USE EXAMPLES

Example A
Sphaerotheca test (cucumber)/protective
Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

In this test, the substance according to the invention mentioned in Example (1) exhibits, at an application rate of 100 g/ha, an efficacy of 90% or more.

What is claimed is:
1. A compound of the formula (I)

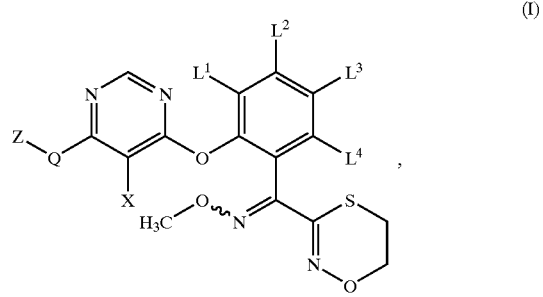

wherein
  Z represents cycloalkyl or cycloalkylalkyl having in each case 3 to 7 carbon atoms in the cycloalkyl moiety and 1 to 4 carbon atoms in the alkyl moiety, each of which may be mono- or disubstituted by halogen, hydroxyl or alkyl;
  represents a heterocyclyl or heterocyclylalkyl selected from the group consisting of thienyl, pyridyl, furyl, thienylmethyl, pyridylmethyl and furylmethyl, each of which may be substituted by halogen or alkyl having 1 to 4 carbon atoms;
  or represents aryl or arylalkyl having in each case 6 to 10 carbon atoms in the aryl moiety and 1 to 4 carbon atoms in the alkyl moiety, each of which may be mono- to tetrasubstituted in the aryl moiety by identical or different substituents selected from the group consisting of:
    halogen, cyano, nitro, amino, formyl, carbamoyl, thiocarbamoyl;
    straight-chain or branched alkyl, alkoxy, alkoxyalkyl, alkylthioalkyl, alkylaminoalkyl, dialkylaminoalkyl, alkylthio, alkylsulphinyl or alkyl sulphonyl having in each case 1 to 8 carbon atoms;
    straight-chain or branched alkenyl or alkenyloxy having in each case 2 to 6 carbon atoms;
    straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
    straight-chain or branched halogenoalkenyl or halogenoalkenyloxy having in each case 2 to 6 carbon atoms and 1 to 11 identical or different halogen atoms;
    straight-chain or branched alkylamino, dialkylamino, alkylcarbonyl, alkoxycarbonyl, alkylaminocarbonyl, dialkylaminocarbonyl, arylalkylaminocarbonyl, alkenylcarbonyl or alkinylcarbonyl, having 1 to 6 carbon atoms in the respective hydrocarbon chains;
    cycloalkyl or cycloalkyloxy having in each case 3 to 6 carbon atoms;
    doubly attached alkylene having 3 or 4 carbon atoms, oxyalkylene having 2 or 3 carbon atoms or dioxyalkylene having 1 or 2 carbon atoms, each of which is optionally mono- to tetrasubstituted by identical or different substituents selected from the group consisting of fluorine, chlorine, oxo, methyl, trifluoromethyl and ethyl;

and the grouping

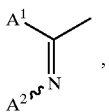

in which
A² represents hydrogen or alkyl having 1 to 4 carbon atoms or cycloalkyl having 3 to 6 carbon atoms and
A² represents hydroxyl, amino, methylamino, methyl, phenyl, benzyl, alkoxy, alkylamino, dialkylamino having 1 to 4 carbon atoms in the respective alkyl chains;

Q represents oxygen or sulphur,

X represents fluorine, chlorine or bromine, and $L^1$, $L^2$, $L^3$ and $L^4$ are identical or different and, independently of one another, each represents hydrogen, halogen, cyano, nitro, represents alkyl, alkoxy, alkylthio, alkylsulphinyl or alkylsulphonyl having in each case 1 to 6 carbon atoms and being in each case optionally substituted by 1 to 5 halogen atoms.

2. The compound of claim 1 wherein

Z represents cyclopentyl or cyclohexyl, each of may be mono- or disubstituted by fluorine, chlorine, methyl, ethyl or hydroxyl;
represents thienyl, pyridyl, furyl, thienylmethyl, pyridylmethyl or furylmethyl, each of which may be substituted by methyl, ethyl, fluorine, chlorine or bromine;
or, represents phenyl or benzyl, each of which may be mono- to tetrasubstituted by identical or different substituents selected from group consisting of:
fluorine, chlorine, bromine, cyano, nitro, amino, formyl, carbamoyl, thiocarbamoyl;
methyl, ethyl, n- or i-propyl, n-, i-, s- or t-butyl, methoxymethyl;
methoxy, ethoxy, n- or i-propoxy;
methylthio, ethylthio, n- or i-propylthio, methylsulphinyl, ethylsulphinyl, methylsulphonyl or ethylsulphonyl;
methylaminomethyl, dimethylaminomethyl;
vinyl, allyl, 2-methylallyl, propene-1-yl, crotonyl, propargyl, vinyloxy, allyloxy, 2-methylallyloxy, propene-1-yloxy, crotonyloxy, propargyloxy;
trifluoromethyl, trifluoroethyl;
difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl;
methylamino, ethylamino, n- or i-propylamino, dimethylamino, diethylamino;
acetyl, propionyl, methoxycarbonyl, ethoxycarbonyl, methylaminocarbonyl, ethylaminocarbonyl, dimethylaminocarbonyl, diethylaminocarbonyl, acryloyl, propioloyl;
cyclopentyl, cyclohexyl;
doubly attached propanediyl, ethyleneoxy, methylenedioxy, ethylenedioxy, each of which may be mono- to tetrasubstituted by identical or different substituents selected from the group consisting of fluorine, chlorine, oxo, methyl and trifluoromethyl; and the grouping

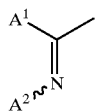

where
A¹ represents hydrogen or methyl and
A² represents hydroxyl, methoxy, ethoxy, amino, methylamino, methyl, phenyl or benzyl;

Q represents oxygen,

X represents fluorine or chlorine and $L^1$, $L^2$, $L^3$ and $L^4$ are identical or different and, independently of one another, each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

3. A method for controlling undesirable microorganisms, comprising allowing an microbicidally effective amount of a compound of claim 1 to act on said microorganisms and/or their habitat.

4. A process for preparing compounds of the formula (I) as defined in claim 1, comprising reacting a 3-(2-hydroxyphenyl)-3-methoxyiminomethyl-oxathiazine of the formula (II)

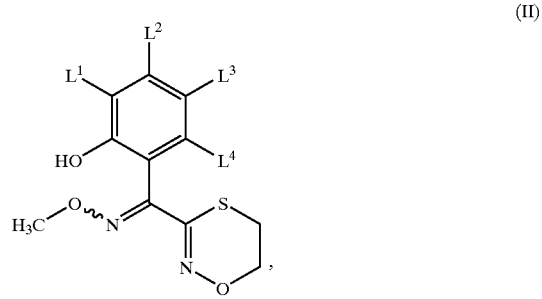

(II)

in which
$L^1$, $L^2$, $L^3$ and $L^4$ are each as defined in claim 1 with a substituted halogenopyrimidine of the formula (III)

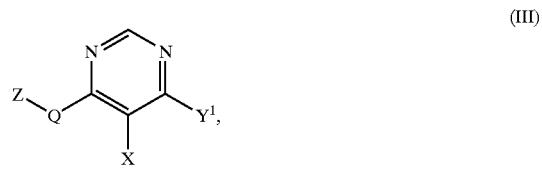

(III)

in which
Z, Q and X are each as defined in claim 1 and
$Y^1$ represents halogen,
if appropriate in the presence of a member selected from the group consisting of a diluent, an acid acceptor, a catalyst, or mixtures thereof.

5. A compound of the formula (IV)

(IV)

in which
L$^1$, L$^2$, L$^3$ and L$^4$ are each as defined in claim 1 and
Y$^2$ represents halogen.

6. A microbicidal composition comprising a microbicidally effective amount of a compound of claim 1 and a member selected from the group consisting of an extender, a surfactant, and mixtures thereof.

7. The compound formula:

\* \* \* \* \*